(12) United States Patent
Smith et al.

(10) Patent No.: US 12,256,933 B2
(45) Date of Patent: Mar. 25, 2025

(54) DEVICES, SYSTEMS, AND METHODS FOR FORMING AN OPENING BETWEEN BODY LUMENS

(71) Applicant: Boston Scientific Scimed, Inc., Maple Grove, MN (US)

(72) Inventors: Amanda L. Smith, Boston, MA (US); John T. Favreau, Spencer, MA (US); Travis Henchie, Worcester, MA (US); Joseph W. King, Franklin, MA (US); Lauren Lydecker, Millbury, MA (US); Andrew Pic, Northboro, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1073 days.

(21) Appl. No.: 17/178,903

(22) Filed: Feb. 18, 2021

(65) Prior Publication Data
US 2021/0259691 A1    Aug. 26, 2021

Related U.S. Application Data

(60) Provisional application No. 62/979,181, filed on Feb. 20, 2020.

(51) Int. Cl.
| | |
|---|---|
| *A61B 17/11* | (2006.01) |
| *A61F 2/04* | (2013.01) |
| *A61F 5/00* | (2006.01) |
| *A61B 17/00* | (2006.01) |

(52) U.S. Cl.
CPC ............ *A61B 17/1114* (2013.01); *A61F 2/04* (2013.01); *A61F 5/0076* (2013.01); *A61F 5/0089* (2013.01); *A61B 2017/00292* (2013.01); *A61B 2017/00876* (2013.01); *A61B 2017/1139* (2013.01); *A61F 2002/045* (2013.01)

(58) Field of Classification Search
CPC ................. A61B 17/11; A61B 17/1114; A61B 2017/1117; A61B 2017/1125; A61B 2017/1139; A61B 2017/00876
See application file for complete search history.

(56) References Cited

U.S. PATENT DOCUMENTS

| | | | |
|---|---|---|---|
| 10,130,502 B2 | 11/2018 | Chamorro et al. | |
| 10,307,280 B2 | 6/2019 | Zeiner et al. | |
| 10,420,665 B2 | 9/2019 | Sharma et al. | |
| 10,548,753 B2 | 2/2020 | Rousseau | |
| 2005/0080439 A1* | 4/2005 | Carson .................. | H01F 41/026 606/153 |

(Continued)

*Primary Examiner* — Diane D Yabut
(74) *Attorney, Agent, or Firm* — Seager, Tufte & Wickhem, LLP

(57) ABSTRACT

This disclosure relates generally to the field of devices and procedures for forming an opening between adjacent tissue structures. For example, in an embodiment, a system for forming an opening between body lumens may include a delivery catheter. A first access element may be configured to be positioned against a first body lumen disposed about a distal end of the catheter. A second access element having an outer diameter that substantially matches an outer diameter of the first access element may be disposed about the distal end of the catheter. The second access element may be configured to be positioned against a second body lumen and axially aligned with the first access element. A filament may be electrically coupled to one or both of the first and second access element.

20 Claims, 6 Drawing Sheets

(56) References Cited

U.S. PATENT DOCUMENTS

| | | | |
|---|---|---|---|
| 2008/0051626 A1* | 2/2008 | Sato | A61B 1/00179 |
| | | | 600/101 |
| 2009/0125042 A1* | 5/2009 | Mouw | A61B 17/1114 |
| | | | 606/153 |
| 2013/0325042 A1* | 12/2013 | Fabian | A61B 17/12172 |
| | | | 606/153 |
| 2014/0236064 A1* | 8/2014 | Binmoeller | A61F 5/0076 |
| | | | 604/8 |
| 2016/0100971 A1* | 4/2016 | McGuckin, Jr. | A61F 2/04 |
| | | | 604/8 |
| 2019/0274687 A1* | 9/2019 | Wang | A61B 17/1114 |
| 2019/0298401 A1 | 10/2019 | Gupta et al. | |
| 2019/0343528 A1 | 11/2019 | Fleury et al. | |
| 2019/0343544 A1 | 11/2019 | Tabur et al. | |
| 2019/0357934 A1 | 11/2019 | Borek et al. | |
| 2020/0187946 A1 | 6/2020 | Baron et al. | |
| 2021/0128334 A1 | 5/2021 | Favreau et al. | |

* cited by examiner

DEVICES, SYSTEMS, AND METHODS FOR FORMING AN OPENING BETWEEN BODY LUMENS

PRIORITY

The present application is a non-provisional of and claims the benefit of priority under 35 USC § 119 to U.S. Provisional Application Ser. No. 62/979,181, filed Feb. 20, 2020, the disclosure of which is herein incorporated by reference in its entirety and for all purposes.

FIELD

This disclosure relates generally to the field of devices and procedures for forming an opening between adjacent tissue structures. In particular, the present disclosure relates to endoscopic systems and methods for delivering a device for forming a fistula between body lumens of a patient, such as portions of a gastrointestinal tract ("GI tract").

BACKGROUND

Treating a patient with weight-related or digestive health problems may include a Roux-en-Y or other gastric bypass procedure that may be open, endoluminal, or laparoscopic surgery, wherein the volume and/or pathway between the stomach and the jejunum is reduced. These procedures may be overly complex, time consuming, invasive, irreversible, and/or may involve lengthy recovery times.

Visualization and control of devices being delivered into anatomy beyond the location in front of an endoscope or catheter during an endoscopy procedure may be challenging. For example, medical procedures such as a Roux-en-Y, gastrojejunostomy, hepaticogastrostomy, and gallbladder drainage, may deliver devices on either side of tissue walls. There may be a tendency to lose control of one or more devices during delivery or one or more of the devices may be delivered to an undesirable location. Failure to properly position a device within the appropriate portions of the tissue walls may result in medical complications.

A variety of advantageous medical outcomes may therefore be realized by the embodiments of the present disclosure.

SUMMARY

An aspect of a system for forming an opening between body lumens may include a delivery catheter. A first access element disposed about a distal end of the catheter may be configured to be positioned against a first body lumen. A second access element having an outer diameter that substantially matches an outer diameter of the first access element may be disposed about the distal end of the catheter, the second access element configured to be positioned against a second body lumen and axially aligned with the first access element. A filament may be electrically coupled to the second access element.

In various aspects described here or otherwise within the scope of the present disclosure, a third access element may comprise a magnetic material configured to replace the second access element after the first access element is positioned. A coating may be disposed about one or both of the first access element and the second access element. A stent having a first end and a second end in a deployed configuration each having a flange with a first diameter, and a saddle region between the flanges having a second diameter smaller than the first diameter. The stent may be configured to be deployed within a lumen created by the first access element and the second access element being axially aligned with each other. The second access element may comprise an annulus shape. The filament may be wound about the second access element in a single direction about the second access element. The filament may be a grasper. The first body lumen may be the stomach and the second body lumen may be the jejunum. The filament may be reversibly coupled to the first access element. The system may include a light-emitting source configured to be illuminated proximate the first access element such that light emitted from the light-emitting source is observable across tissue In an aspect, a system for forming an opening between body lumens may include a catheter having a delivery filament. A first access element may be deployable from about a distal end of the catheter. A second access element may be deployable from about the distal end of the catheter. The second access element may comprise a magnetic material. The second access element may have a diameter that substantially matches a diameter of the first access element.

In various aspects described here or otherwise within the scope of the present disclosure, a coating may be disposed about each of the first access element and the second access element. The coating has a thickness such that when the first access element and the second access element pinch tissue of the body lumens therebetween, a portion of the coating of each of the first access element and the second access element may pinch the tissue at a diameter larger than the diameters of the first access element and the second access element. The first access element and the second access element may be spaced apart from each other about the catheter. A spacer may be between the first access element and the second access element. The first access element may comprise a magnetic material and the first access element and the second access element may be oriented about the catheter such that like magnetic poles of each of the first access element and the second access element are adjacent each other. A stent may have a first end and a second end. Each of the first and second end of the stent in a deployed configuration may each have a flange with a first diameter and a body between the flanges having a second diameter smaller than the first diameter. The stent may be configured to be deployed within a fistula created by the first access element and the second access element. The first access element and the second access element may each be an anulus, a flat anulus, a disc, or an oblong-shaped body.

In an aspect, a method of forming an opening between tissue of a first body lumen and a second body lumen may include delivering a first access element into the first body lumen. A second access element comprising a magnetic material may be delivered into the second body lumen. The second access element may be oriented such that it magnetically attracts the first access element across the tissue of the first body lumen and the second body lumen. A user may axially align the first and second access elements such that necrosis of the tissue between the first access element and second access element forms the opening between the first and second body lumens.

In various aspects described here or otherwise within the scope of the present disclosure, delivering the first access element may be performed with a first filament coupled to the first access element. Delivering the first access element may be performed via peristalsis distally past the pyloric sphincter. The first access element may be observed using fluoroscopy or a visible light emitting source within the first body lumen. Delivering the first access element may be performed with a first filament coupled to the first access element. Delivering the second access element may be performed with a second filament coupled to the second access element. The second access element may be electromagnetic and is magnetized via the second filament.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
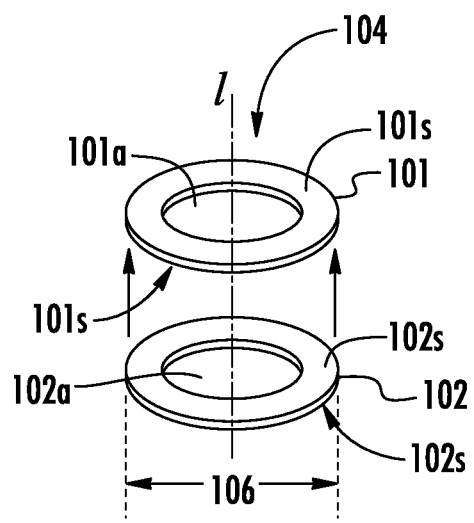
FIG. 1A illustrates a system for forming an opening between body lumens including a first access element and a second access element, according to an embodiment of the present disclosure.

The present disclosure is not limited to the particular embodiments described herein. The terminology used herein is for the purpose of describing particular embodiments only and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to embodiments of a medical device delivery system for delivering a medical device within a specific portion the GI tract for a particular purpose (e.g., to impact metabolism and affect weight loss), it should be appreciated that such embodiments may be used to deliver a variety of configurations of such medical devices into a variety of different body lumens and/or passageways, for a variety of different purposes, including, for example, anal access to the transverse colon, ascending colon or ileum, Roux-en-Y procedures, jejunocolonic bypass procedures, jejunoileal bypass procedures, gastrectomy procedures, biliopancreatic diversion with duodenal switch (BPD-DS) procedures, gastrojejunostomy procedures, segmental colonic resection procedures, and the like.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. The term "or" is generally employed in its sense including "and/or" unless the content clearly dictates otherwise.

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

A medical procedure that may reduce and/or delay absorption of digestible material by a GI tract may include providing an alternative route for digestion materials through the stomach into, e.g., the jejunum, substantially bypassing the duodenum. An alternative route may allow passage of materials without significant (or substantially limited) contact with intestinal tissues and/or digestive enzymes or like fluids along that portion of the GI tract. Such restricted, limited, or delayed interaction between materials (e.g., stomach chyme) and the GI tract may assist with alleviating or at least positively impacting weight (obesity) and/or diabetic complications.

Although the present disclosure includes description of openings or fistulas formed in the GI tract to affect weight and absorption, the devices, systems, and methods herein could be implemented along various other portions of the GI tract, or between lumens outside of the GI tract, and for various other drainage and/or conduit purposes.

Referring to FIG. 1A, an embodiment of a fistula forming system is illustrated including a first access element 101 and a second access element 102 each having a substantially matching outer diameter 106. The elements 101, 102 are illustrated with substantially flat (i.e., planar) surfaces 101s, 102s, however, in various embodiments the elements 101, 102 may form various shapes including rings, annuli, torii, discs, a combination thereof, or the like. Additionally, the access elements 101, 102 may be similar or dissimilar with each other. The access elements 101, 102 each include a first aperture 101a and a second aperture 102a respectively therethrough each of the access elements 101, 102. Although the access elements 101, 102 are illustrated with apertures 101a, 102a, in various embodiments, one or both of the access elements 101, 102 may not have an aperture 101a, 102a (e.g., a disc, a spheroid, an ovoid, or the like). One or both of the access elements 101, 102 may be magnetic, as permanent magnets or electromagnets, such that the access elements 101, 102 are magnetically attracted to each other. The access elements 101, 102 may be attracted to each other such that the surfaces 101s, 102s are brought near or into contact with each other. In embodiments where the surfaces 101s, 102s are substantially flat, the interface between the surfaces 101s, 102s may be larger than in embodiments where one or all of the surfaces 101s, 102s are shapes other than substantially flat (e.g., less contact area between surfaces of a torus than a flat disc). As the access elements 101, 102 are magnetically attracted toward each other, they may be axially aligned along a shared longitudinal axis €. The longitudinal axis € may extend through the apertures 101a, 102a forming a lumen 104 therethrough. In various embodiments, a portion of the elements 101, 102 may be magnetic while other portion(s) are not, e.g., such that the elements 101, 102 align with each other in a particular orientation. In various embodiments, one element 101, 102 may be magnetic while the other is not. In various embodiments, an aperture 101a, 102a may have a diameter of any amount, for example, about 5 mm to about 25 mm within a body lumen such as the small intestine but can be smaller or larger, for example, larger within the stomach. In various embodiments, a width of a surface 101s, 102s may have any width, for example, about 1 mm to about 15 mm, for example, about 10 mm to about 15 mm. In various embodiments, an access element 101, 102 may have a thickness along the longitudinal axis € of any amount, for example, about less than 1 mm to about 10 mm.

Figure 1B:
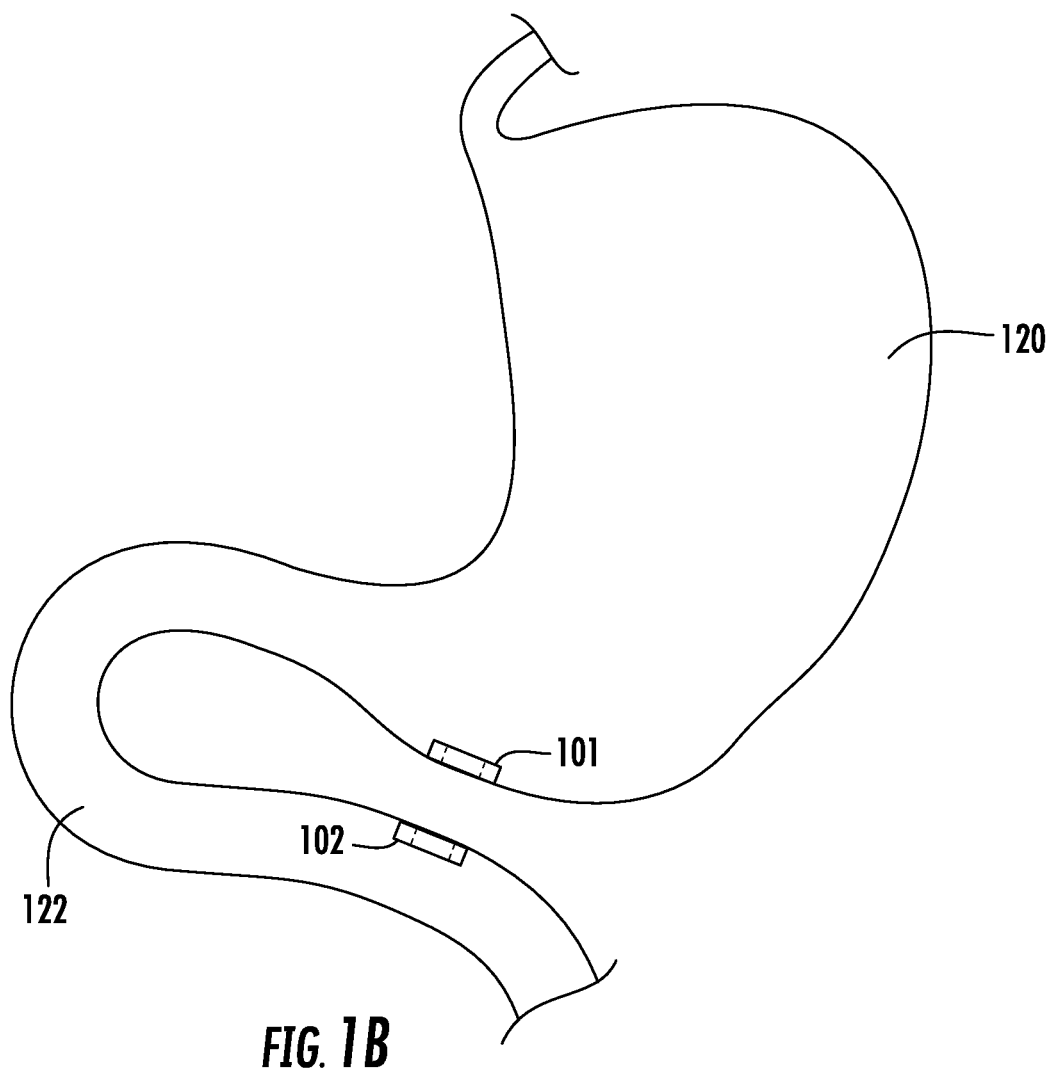
FIG. 1B illustrates the system of FIG. 1A being delivered into the GI tract.

Referring to FIG. 1B, the access elements 101, 102 may be delivered into one or more body lumens for forming a fistula between the body lumens. In FIG. 1B, the first access element 101 is delivered into the stomach 120, e.g., through the esophagus, and the second access element 102 is delivered into the jejunum 122, e.g., distally further through the duodenum. The access elements 101, 102 may be manipulated (e.g., by manipulating one or more filament(s) described herein or additional medical instruments) such that they are substantially proximate each other (e.g., such that the access elements 101, 102 succumb to magnetic attraction with each other across or through tissues of the body lumen(s)) at desired delivery locations (e.g., where a medical professional would like to establish an additional lumen in the GI tract). In FIG. 1B, the access elements 101, 102 are delivered adjacent the walls of the stomach 120 and the jejunum 122, respectively.

Figure 1C:
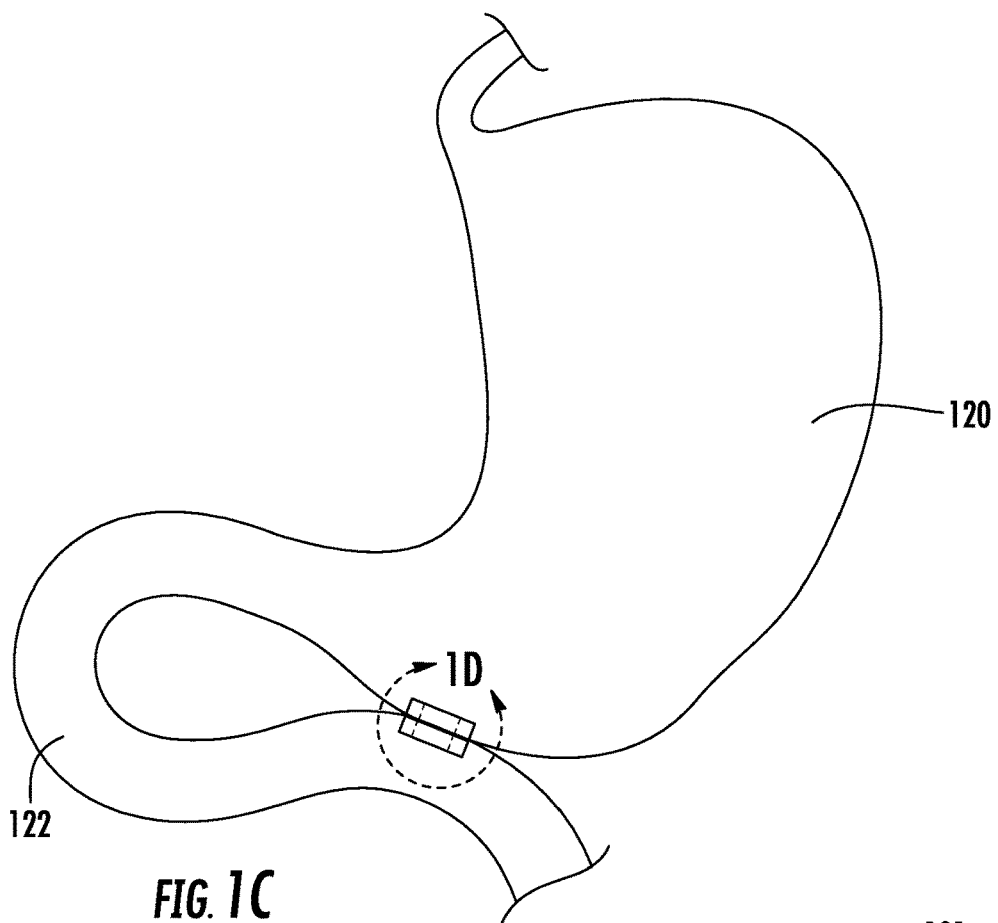
FIG. 1C illustrates the system of FIGS. 1A and 1B delivered in the GI tract.
Figure 1D:
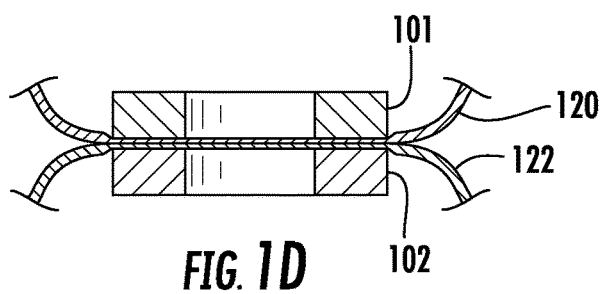
FIG. 1D illustrates a closer view of the system of FIG. 1C, with the access elements shown in cross-section.

Referring to FIGS. 1C and 1D, the first and second access elements 101, 102 are magnetically attracted to each other (i.e., via a magnetic field of one or both of the elements 101, 102) across the wall of the stomach 120 and the jejunum 122 such that the tissue of the wall of the stomach 120 and the jejunum 122 are brought into contact with each other. Between the orientation of FIGS. 1B and 1C, the first and second access elements 101, 102 are proximate each other enough and/or the magnetic forces strong enough such that the first and second access elements 101, 102 are attracted and pulled to each other across the stomach 120 and jejunum 122. The first and second access elements 101, 102 are shown aligned axially and are pinching the tissue of the stomach 120 and the jejunum 122.

Figure 1E:
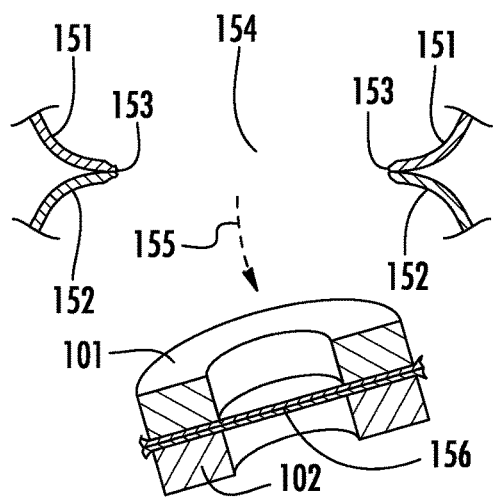
FIG. 1E illustrates the system of FIGS. 1A-1D forming a fistula with the access elements shown in cross-section.

Referring to FIG. 1E, the system of FIGS. 1A-1D may create a fistula by access elements 101, 102 compressing and/or fixing a first body lumen tissue 151 to a second body lumen tissue 152 resulting in the tissues 151, 152 apposing each other at points 153. The tissues 151, 152 may be compressed with sufficient force and/or for a sufficient time such that the tissues adhere to each and necrosis occurs. In various embodiments, described here only to provide examples, cell death may begin about 2 hours or about 3 hours of compression from ischemia or a lack of blood flow. Necrosis of these cells and/or tissues may begin about within the first day. Healing of tissue of these cells may take about 2 weeks. Formation of a mature anastomosis may take as long as about 8 weeks. Larger compression forces between elements 101, 102 may accelerate necrosis and related timeframes while lower compression forces may decelerate necrosis and related timeframes. Borders of the necrotic tissues may adhere together forming a lumen 154 across the tissues between the borders. The first and second tissues 151, 152 are not limited to different organs. For example, a region of an organ may be referred to as the first tissue or body lumen and a different region of the same organ may be referred to as the second tissue or body lumen, so as to include fixing these two regions within the same organ. For example, a treatment to drain a blocked common biliary duct may include compressing it against a duodenum and thus causing both organs to communicate with each other.

In various embodiments, after creation of the lumen 154 of the fistula, the access elements 101, 102 may remain in place about the fistula or they may move through the tissue(s) 151, 152 with necrotic tissues 156 compressed between the elements 101, 102 via the lumen 154 of the fistula and passed through the patient (e.g., as illustrated with arrow 155). The access elements 101, 102 may stay in place to keep the tissue(s) 151, 152 of the fistula in contact with each other or a single tissue itself. The access elements 101, 102 may stay in place to provide structure and/or support for another device delivered through the fistula.

Figure 2A:
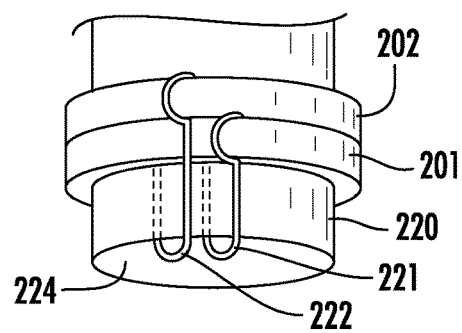
FIG. 2A illustrates a system for forming an opening between body lumens including a first access element and a second access element disposed about a delivery catheter, according to an embodiment of the present disclosure.

Referring to FIG. 2A, a system for forming an opening between body lumens is illustrated including a delivery catheter 220, which may be a catheter, a delivery tube, an endoscope, a cap, or the like. A first access element 201 is disposed about a distal end of the catheter 220. A second access element 202 is disposed about the distal end of the catheter 220 proximal to the first access element 201. Although FIG. 2A illustrates two access elements 201, 202, any number of access elements may be disposed about the catheter 220, e.g., 0, 1, 3, 4, 5, 6, 8, 10, 15, 20, 50, 100, or the like. Additional access elements may be disposed about the catheter 220 for additional procedures or for creating additional fistulas in the same procedure. The system is illustrated in a delivery configuration such that the system may be inserted and/or translated into a scope and/or a patient and into or toward one or more body lumens. The catheter 220 includes a first delivery filament 221. The first delivery filament 221 extends through a lumen 224 of the catheter 220 and out of the distal end of the catheter 220. A distal portion of the first filament 221 is disposed about the first access element 201. A second filament 222 also extends through the lumen 224 and a distal portion of the second filament 222 is disposed about the second access element 202. The first filament 221 may be wrapped, adhered, tied, looped, woven, grasped, or the like about or to one or more of the access elements 201, 202. Although two filaments 201, 202 are illustrated, any number of filaments may be used, e.g., 0, 1, 3, 4, 5, 6, 8, 10, 15, 20, 50, 100, or the like. In various embodiments, a filament 221, 222 may be disposed about one or more access elements 201, 202 of a system. The filaments 221, 222 may be disposed about the access elements 201, 202 such that a proximal translation of the filaments 221, 222 through the catheter 220 pulls the access elements 201, 202 distally along and off of the catheter 220.

In various embodiments, one or more access elements may comprise a magnetic material. Magnetic access elements may be loaded about a catheter in a delivery configuration such that like poles are adjacent each other or magnetic access elements may be loaded about a catheter such that opposing poles are adjacent each other. Magnetic access elements loaded with like poles adjacent may not be magnetically attracted to each other and/or may be repelled from each other such that deployment of one or more of the access elements from the catheter may require less force (i.e., from a filament or the like) than access elements loaded about a catheter with opposing poles adjacent each other. Additionally, or in the alternative, the access elements may be spaced apart from each other and/or a spacer element (e.g., a non-metallic spacer element) may be disposed between access elements configured to reduce magnetic attraction between access elements. Magnetic access elements may be magnetically attracted to each other across tissue of one or more body lumens when deployed. In some embodiments, one or more access elements may be electromagnets, such that magnetic attraction between the access elements may not occur until a magnetic field is generated. This may allow the access elements to be positioned as desired prior to generating a magnetic field to minimize misalignment.

Figure 2B:
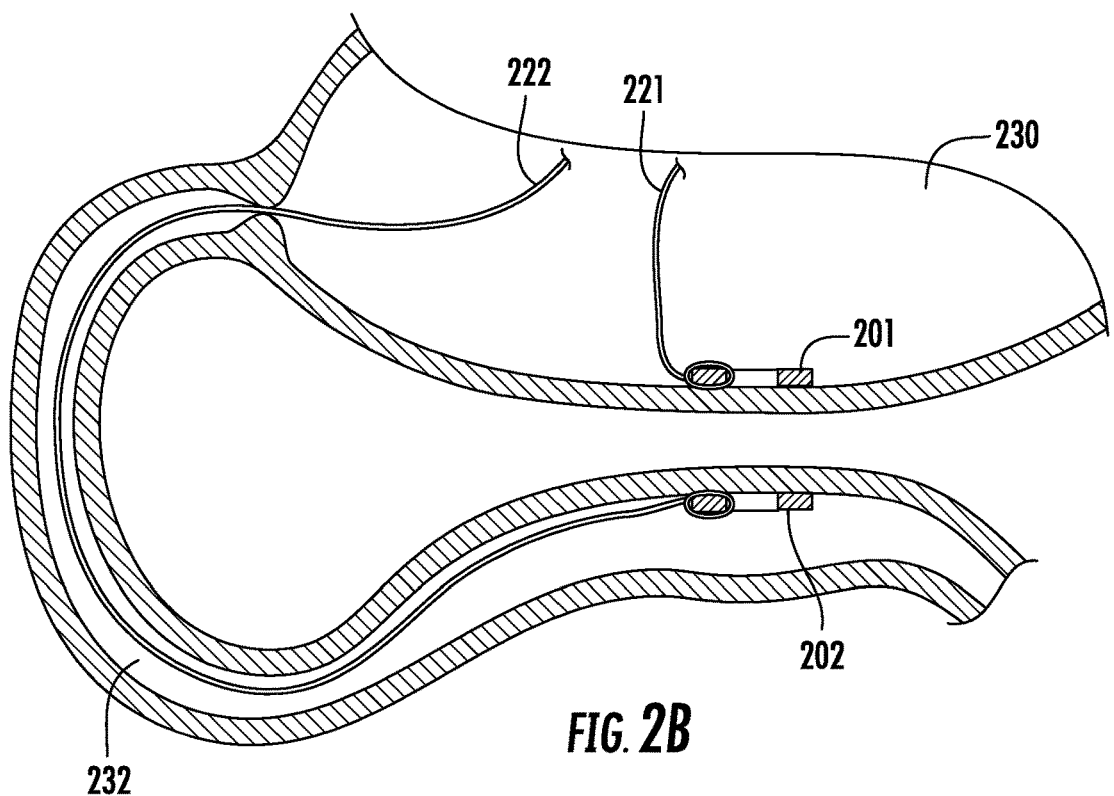
FIG. 2B illustrates the system of FIG. 2A being delivered into the GI tract.

Referring to FIG. 2B, the access elements 201, 202 from FIG. 2A are illustrated being deployed within the stomach 230 and jejunum 222. The first access element 201 may be deployed from the catheter 220 in the delivery configuration illustrated in FIG. 2A by proximally translating the first filament 221 through the lumen 224 catheter 220 such that a distal end of the first filament 221 disposed about the first access element 201 moves the first access element 201 distally from about the catheter 220. The first filament 221 is manipulated to orient the first access element 201 toward and/or against a tissue wall of the stomach 230 body lumen. The second access element 202 may be deployed from the catheter 220 in the delivery configuration by proximally translating the second filament 222 through the lumen 224 of the catheter 220 such that a distal end of the second filament 222 disposed about the second access element 202 moves the second access element 202 distally from about the catheter 220. The second filament 222 is manipulated to orient the second access element 202 toward a body lumen opening of the jejunum 232 and/or against a tissue wall of the jejunum 232. Natural peristalsis of one or more of body lumens of a patient may assist with deploying or orienting the access elements 201, 202 by muscles of the GI tract moving one of the access elements 201, 202 along the GI tract toward the other access element 201, 202 (e.g., across tissue). One or more of the access elements 201, 202 may be oriented such that the access elements 201, 202 are proximate each other across one or more tissues. In various embodiments, the first and second access elements 201, 202 may be magnetic. The first and second access elements 201, 202 may be used to locate each other and to bring tissues towards each other. A third access element, providing a larger magnetic force than the first two access elements 201, 202, may be delivered in addition to or in place of one of the access elements 201, 202 to compress the tissues for necrosis.

Figure 2C:
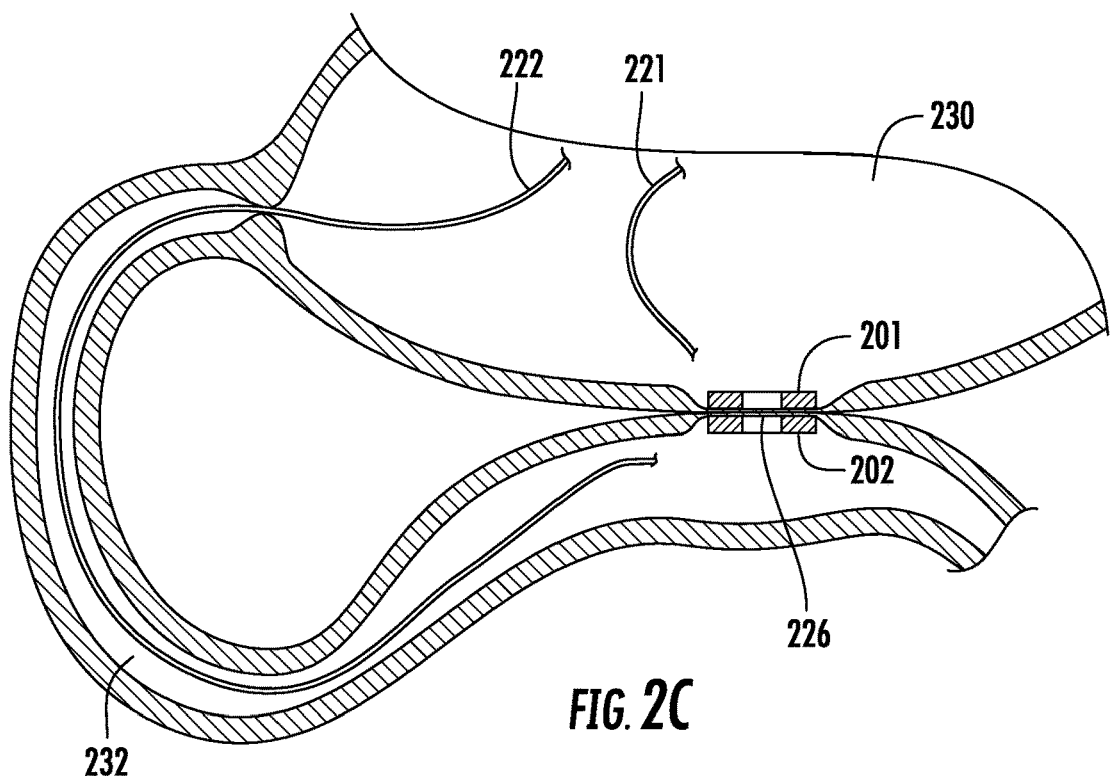
FIG. 2C illustrates the system of FIGS. 2A and 2B being delivered into the GI tract.

Referring to FIG. 2C, the access elements 201, 202 of FIGS. 2A and 2B are illustrated in a deployed configuration. The access elements 201, 202 are oriented proximate each other between FIGS. 2B and 2C such that the access elements 201, 202 are magnetically attached to each other across tissues of the stomach 230 and the jejunum 232. The access elements 201, 202 are compressing a portion 226 of the tissues of the stomach 230 and the jejunum 232 such that the portion 226 can undergo necrosis. The filaments 221, 222 are detached from the access elements 201, 202 and removed from the patient. The filaments 221, 222 may be detached by, e.g., severing, cutting, untying, degrading, melting, ungrasping, or the like. Alternatively, the filaments 221, 222 may be left within the patient along with the access elements 201, 202.

In various embodiments, access elements may be left within a patient compressing one or more tissues of one or more body lumens. A portion of the one or more tissues may undergo necrosis as the portion is compressed as described herein. The portion of tissue may separate away from the body lumen(s) during or after necrosis. The access elements may also fall away along with or after the portion of the tissue separates away from the body lumen(s). The access elements may be passed naturally by the patient or one or more of the access elements may be retrieved by a medical professional.

Figure 3A:
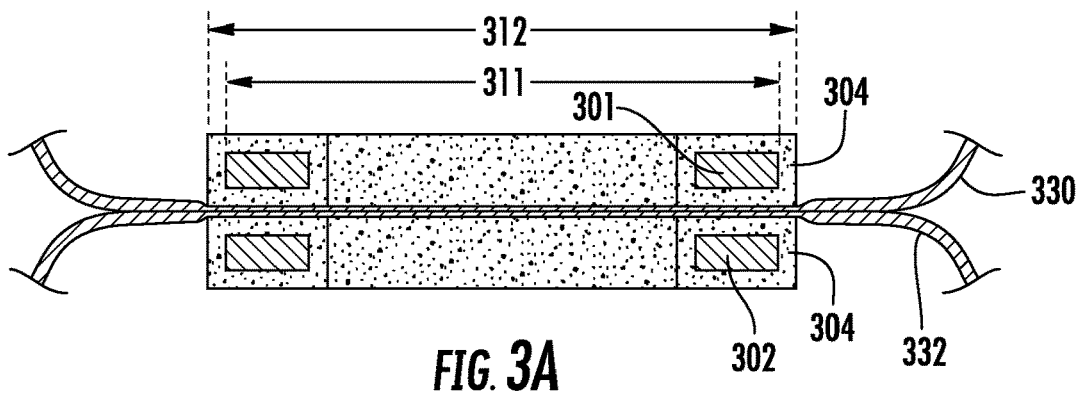
FIG. 3A illustrates a system for forming an opening between body lumens with a first access element and a second access element that are coated, according to an embodiment of the present disclosure.

Referring to FIG. 3A, a first access element 301 and a second access element 302 are magnetically attracted to each other across a first tissue 330 and a second tissue 332. The first and second tissues 330, 332 may be part of the same body lumen or may be part of separate body lumens. The first and second tissues 330, 332 are compressed between the access elements 301, 302 and are undergoing necrosis. A biodegradable coating 304 is disposed about each of the first access element 301 and the second access element 302. The access elements 301, 302 each have a first outer diameter 311 and the biodegradable coating 304 about the access elements 301, 302 each have a second outer diameter 312 that is larger than the first outer diameter 311. The access elements 301, 302 are illustrated in a deployed configuration in FIG. 3A. The tissues 330, 332 are being compressed between the biodegradable coating 304 at a diameter about the size of the second outer diameter 312. Over time, the tissues 330, 332 may undergo necrosis and the biodegradable coating 304 may degrade.

Figure 3B:
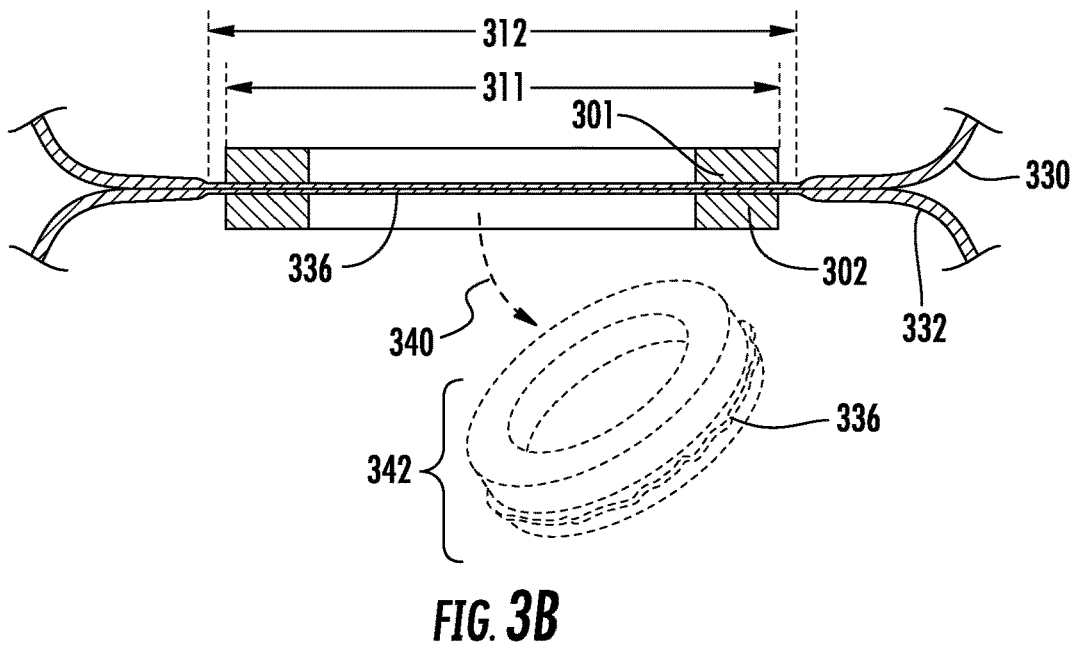
FIG. 3B illustrates the system of FIG. 3A with the coating substantially degraded.

Referring to FIG. 3B, the access elements are shown with the biodegradable coating 304 degraded. The tissues 330, 332 are undergoing necrosis such that portions 336 of the tissues 330, 332 will separate from a remainder of the tissues 330, 332 at about a diameter of the second outer diameter 312. During or after necrosis, the portion 336 and the access elements 301, 302 may separate away from the tissues 330, 332 as indicated by the arrow 340 and the phantom position 342 of the portions of tissues and elements.

Figure 4:
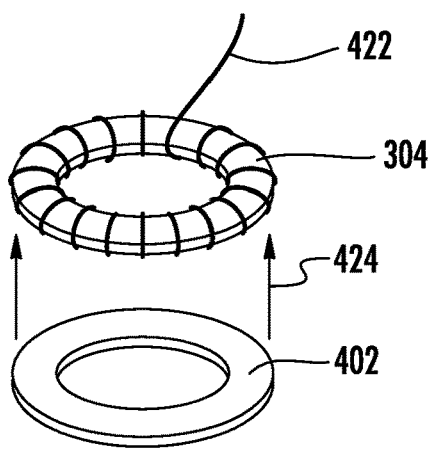
FIG. 4 illustrates a system for forming an opening between body lumens including an electroactive filament, according to an embodiment of the present disclosure.

Referring to FIG. 4, an embodiment of a system for forming an opening between body lumens is illustrated including a first access element 401 and a second access element 402. A filament 422 is electrically coupled to the first access element 401. The filament 422 is wound about the first access element 401 in a single direction about an anulus-like shape of the first access element 401. The filament 422 may be energized, creating an electromagnetic field that attracts the first and second access elements 401, 402 together (e.g., as indicated by the arrows 424. The access elements 401, 402 may be attracted to each other across one or more tissues for compressing the one or more tissues, inducing necrosis, and creating a fistula. The access elements 401, 402 may be released from each other by deactivating the filament 422 such that the access elements 401, 402 may separate from each other. For example, a medical professional may magnetically couple the access elements 401, 402 across one or more tissues by activating the filament 422. However, the medical professional may desire that the access elements 401, 402 be located at a different portion of the one or more tissues. The medical professional may separate the access elements 401, 402 from each other by deactivating the filament 422 and relocating one or both of the access elements 401, 402 to another portion of the one or more tissues. In various embodiments, a medical professional may locate one or more access elements 401, 402 by activating the filament 422 to magnetically attract one access element to the other. In various embodiments, a medical professional may manipulate the second access element 402 by electrically activating the filament 422 such that the second access element 402 is moved from a first position to a second position towards the filament 422 and the first access element 401. In various embodiments, one or more additional filaments that may or may not be electrically conductive may be used, e.g., a second filament coupled to the second access element 402.

Figure 5:
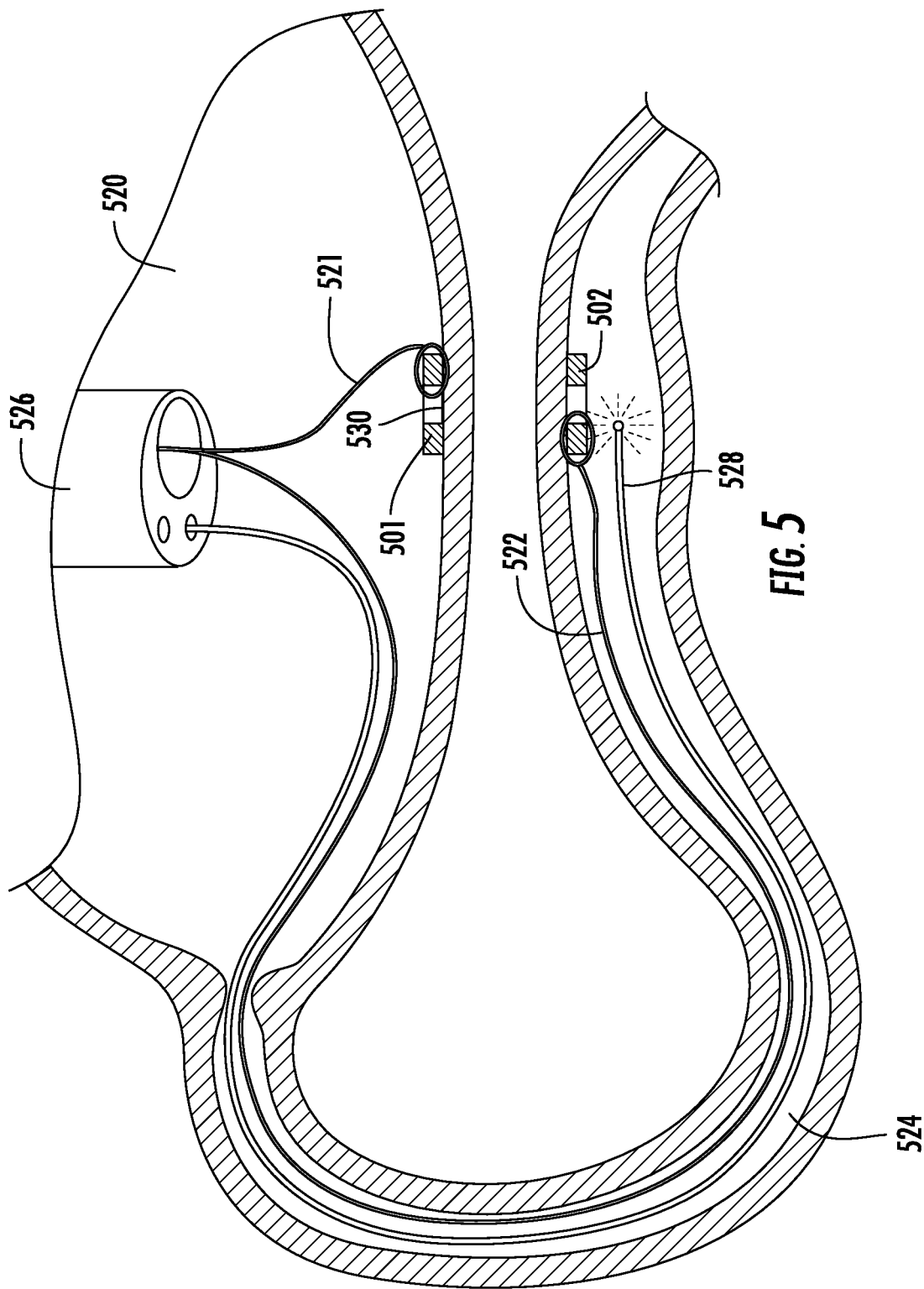
FIG. 5 illustrates a system for forming an opening between body lumens including an illuminating device, according to an embodiment of the present disclosure.

Referring to FIG. 5, an embodiment of a system for forming an opening between body lumens is illustrated including a first access element 501 coupled to a first filament 521 and a second access element 502 coupled to a second filament 522. The first access element 501 is delivered against a tissue of the stomach 520 and the second access element 502 is delivered against a tissue of the jejunum 524. The access elements 501, 502 are delivered and visualized through an endoscope 526. A light-emitting source 528 may be delivered from the endoscope 526 along with or towards the second access element 502. The second access element 502 may not be visible in the delivered configuration by the endoscope 526 (e.g., with the second access element 502 in the jejunum 524 and the endoscope 526 in the stomach 520). The light-emitting source 528 may be illuminated while proximate the second access element 502 such that the light and/or a silhouette of the second access element 502 may be visible via the endoscope 526 through the tissue of the jejunum 524 and the stomach 520 at location 530. The light-emitting source 528 may be used to locate and/or position one or more of the access elements 501, 502 with respect to each other and/or anatomies.

Figure 6:
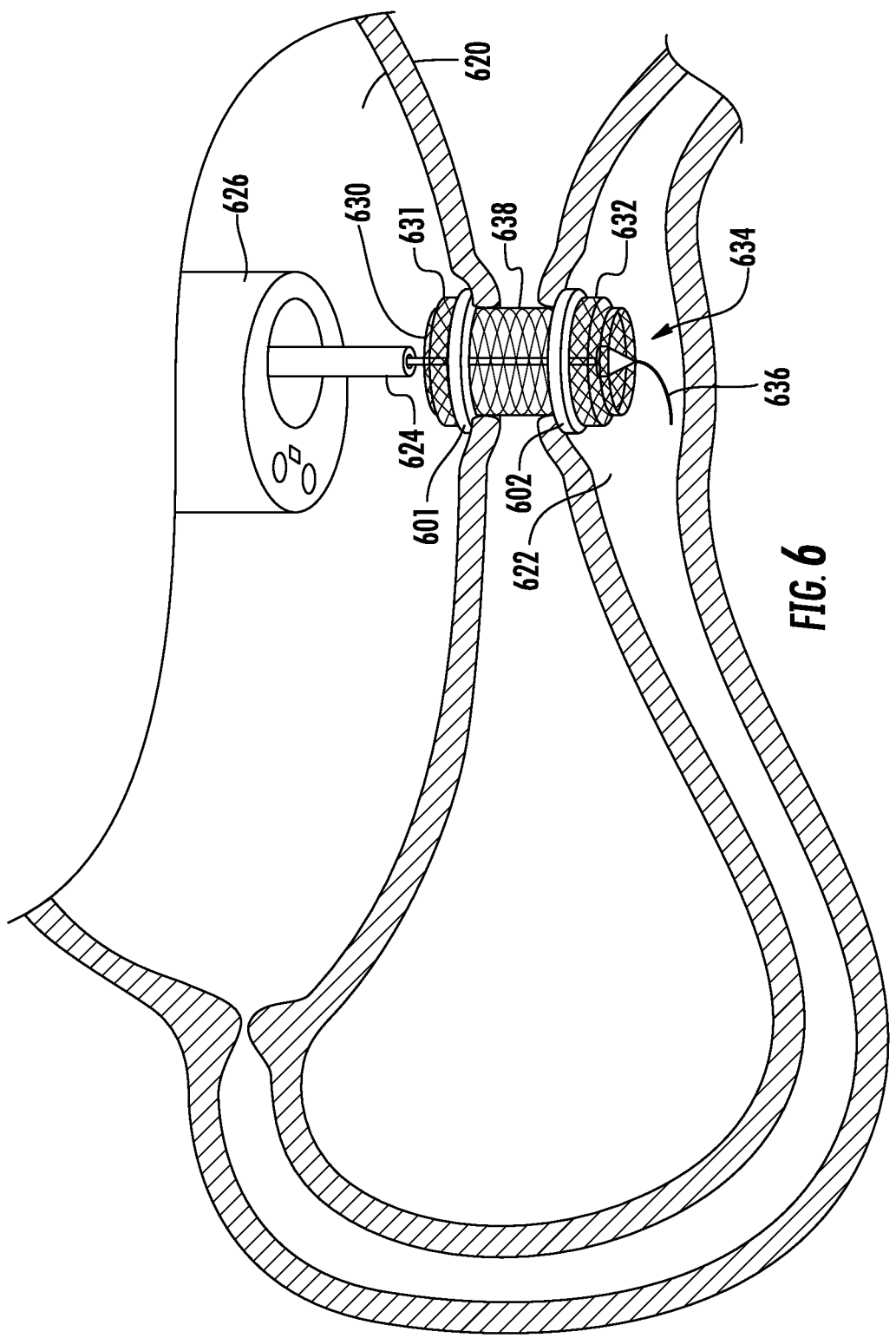
FIG. 6 illustrates a system for forming an opening between body lumens including a stent, according to an embodiment of the present disclosure.

Referring to FIG. 6, an embodiment of a system for forming an opening between body lumens is illustrated including a first access element 601 delivered against a tissue of the stomach 620 and a second access element 602 delivered against a tissue of the jejunum 622. The access elements 601, 602 are magnetically attracted towards each other and move tissue of the stomach 620 and the jejunum 622 toward each other. Prior to necrosis, during necrosis, after necrosis, after the access elements 601, 602 are moved away from the tissues, or after healing (e.g., adhering) borders of the necrotic tissues together, a guidewire 636 and or a stent 630 may be delivered via an endoscope 626 and a catheter 624 through the stomach 620 and the jejunum 622 forming a lumen 634. The stent 630 includes flanges 632 at ends of the stent 630 in the deployed configuration. The stent 630 is a braided self-expanding stent with a reduced diameter in a delivery configuration within a working channel such that the flanges 631, 632 may be substantially reduced or non-existent in shape. Each of the flanges 632 has a diameter that is wider than a remainder of the stent 630, including a saddle region 638 between the flanges 632. The saddle region 638 may fit through the internal diameters of the access elements 601, 602 and the flanges 632 may be wider than the internal diameters of the access elements 601, 602. The stent 630 is deployed through and/or forms the lumen 634 with the distal flange 632 of the stent 630 deployed into the jejunum 622 and the proximal flange 632 deployed into the stomach 620. The access elements 601, 602 may move the tissues of the stomach 620 and the jejunum 622 toward each, allowing the stent 630 to travel less of a distance and have a shorter axial length between the stomach 620 and the jejunum 622 than without the access elements 601, 602 moving the tissues towards each other. The access elements 601, 602 may provide support for the flanges 632 during and after delivery of the stent 630, e.g., such as to reduce slipping of the flanges 632 or the like.

In various embodiments described here or otherwise within the scope of the present disclosure, a stent may include tubular barrier and may comprise an elastic material such as silicone, polyethylene terapthelate (PET), nylon, rubber, a combination thereof, or the like. A stent may be a conduit such as to allow passage of materials through a lumen of the stent. Due to the resilient flexibility of a stent, smooth muscles may contract in peristaltic waves to translate materials through the stent.

In various embodiments, a method for forming an opening between tissue of a first body lumen and a second body lumen may include delivering a first access element into a first body lumen. A second access element comprising a magnetic material may be delivered into a second body lumen. The second access element may be oriented and/or aligned such that it magnetically attracts the first access element across tissue of the first body lumen and the second body lumen. A user may axially align the first and second axis element such that necrosis of the tissue between the first access element and second access element forms the opening between the first and second body lumens. Delivering the first access element may be performed with a first filament coupled to the first access element. Delivering the first access element may be performed via peristalsis distally past the pyloric sphincter. The first access element may be observed using fluoroscopy or a visible light emitting source within the first body lumen. Delivering the first access element may be performed using a first filament coupled to the first access element. Delivering the second access element may be performed using a second filament coupled to the second access element. In various embodiments, one or more access elements may be manipulated by a medical tool such as a grasper instead of or in addition to a filament. The second access element may be electromagnetic and activated via the second filament.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A system for forming an opening between body lumens, the system comprising:
    a delivery catheter;
    a first access element encircling an exterior surface of a distal end of the delivery catheter and configured to be positioned against a first body lumen;
    a second access element encircling an exterior surface of the distal end of the delivery catheter and having an outer diameter that substantially matches an outer diameter of the first access element, the second access element configured to be positioned against a second body lumen and axially aligned with the first access element; and
    a filament electrically coupled to the second access element.

2. The system of claim 1, further comprising a third access element comprising a magnetic material configured to replace the second access element after the first access element is positioned.

3. The system of claim 1, further comprising a coating disposed about one or both of the first access element and the second access element.

4. The system of claim 1, further comprising a stent having a first end and a second end, each of the first end and the second end in a deployed configuration having a flange with a first diameter, and a saddle region between the flanges having a second diameter smaller than the first diameter, the stent configured to be deployed within a lumen created by the first access element and the second access element being axially aligned with each other.

5. The system of claim 1, wherein the second access element comprises an annulus shape and the filament is wound about the second access element in a single direction.

6. The system of claim 1, further comprising a grasper configured to manipulate one or both of the first access element and the second access element.

7. The system of claim 1, wherein the first body lumen is the stomach and the second body lumen is the jejunum.

8. A system for forming an opening between body lumens, the system comprising:
    a catheter having a delivery filament extending through a lumen defined by the catheter;
    a first access element inserted into the patient in a configuration external to the catheter and coupled with the delivery filament and deployable from the catheter by pulling proximally on the delivery filament; and
    a second access element inserted into the patient in a configuration external to the catheter and comprising a magnetic material, the second access element having a diameter that substantially matches a diameter of the first access element.

9. The system of claim 8, further comprising a coating disposed about each of the first access element and the second access element.

10. The system of claim 9, wherein the coating has a thickness such that when the first access element and the second access element pinch tissue of the body lumens therebetween, a portion of the coating of each of the first access element and the second access element pinches the tissue at a diameter larger than the diameters of the first access element and the second access element.

11. The system of claim 8, wherein the first access element and the second access element are spaced apart from each other about the catheter.

12. The system of claim 11, further comprising a spacer about the catheter between the first access element and the second access element.

13. The system of claim 8, wherein the first access element comprises a magnetic material and the first access element and the second access element are oriented about the catheter such that like magnetic poles of each of the first access element and the second access element are adjacent each other.

14. The system of claim 8, further comprising a stent having a first end and a second end, each of the first and second end in a deployed configuration having a flange with a first diameter and a body between the flanges having a second diameter smaller than the first diameter, the stent configured to be deployed within a fistula created by the first access element and the second access element.

15. The system of claim 8, wherein the first access element and the second access element are each an annulus, a flat annulus, a disc, or an oblong-shaped body.

16. A method of forming an opening between tissue of a first body lumen and a second body lumen, the method comprising:
    delivering a first access element into the first body lumen over a catheter and by proximally pulling on a first filament coupled to the first access element to deploy the first access element off the catheter;
    delivering a second access element comprising a magnetic material into the second body lumen over the catheter;
    orienting the second access element such that it magnetically attracts the first access element across the tissue of the first body lumen and the second body lumen; and
    axially aligning the first and second access elements such that necrosis of the tissue between the first access element and second access element forms the opening between the first and second body lumens.

17. The method of claim 16, further comprising extending the first filament through a delivery catheter configured to deliver the first access element.

18. The method of claim 17, wherein delivering the second access element is performed with a second filament coupled to the second access element.

19. The method of claim 18, wherein the second access element is electromagnetic and the method further comprises magnetizing the second access element via the second filament.

20. The method of claim 16, further comprising observing the first access element using fluoroscopy or a visible light emitting source within the first body lumen.

* * * * *